United States Patent [19]
Karges et al.

[11] Patent Number: 4,457,866
[45] Date of Patent: Jul. 3, 1984

[54] CHROMOGENIC COMPOUNDS AND THEIR USE AS ENZYME SUBSTRATES

[75] Inventors: Hermann E. Karges; Helmut Heber, both of Marburg an der Lahr; Rainer Uhmann, Kriftel; Volker Teetz, Hofheim am Taunus; Rolf Geiger, Frankfurt am Main, all of Fed. Rep. of Germany

[73] Assignee: Behringwerke Aktiengesellschaft, Marburg an der Lahn, Fed. Rep. of Germany

[21] Appl. No.: 435,610

[22] Filed: Oct. 19, 1982

Related U.S. Application Data

[63] Continuation of Ser. No. 185,007, Sep. 8, 1980, abandoned.

[30] Foreign Application Priority Data

Sep. 10, 1979 [DE] Fed. Rep. of Germany ....... 2936543

[51] Int. Cl.³ ...................... C07C 103/52; C12Q 1/00
[52] U.S. Cl. ................................. 260/112.5 R; 435/4
[58] Field of Search ...................... 260/112.5 R; 435/4

[56] References Cited

U.S. PATENT DOCUMENTS

| | | | |
|---|---|---|---|
| 3,884,896 | 5/1975 | Blomback et al. | 260/112.5 R |
| 3,886,136 | 5/1975 | Claeson et al. | 260/112.5 R |
| 4,016,042 | 4/1977 | Svendsen | 260/112.5 R |
| 4,028,318 | 6/1977 | Aurell et al. | 260/112.5 R |
| 4,119,620 | 10/1978 | Nagatsu et al. | 260/112.5 R |
| 4,137,225 | 1/1979 | Afekenstam et al. | 260/112.5 R |
| 4,279,810 | 7/1981 | Claeson et al. | 260/112.5 R |

OTHER PUBLICATIONS

Gaffney, et al., Haemostasis 7, 109–112, (1978).

*Primary Examiner*—Delbert R. Phillips
*Attorney, Agent, or Firm*—Curtis, Morris & Safford

[57] ABSTRACT

What are disclosed are chromogenic peptides useful as substrates for the detection and determination of enzymes having a hydrolytic action and methods for detecting and determining enzymes with such peptides.

4 Claims, No Drawings

CHROMOGENIC COMPOUNDS AND THEIR USE AS ENZYME SUBSTRATES

This is a continuation of application Ser. No. 185,007, filed Sept. 8, 1980, now abandoned.

The invention relates to chromogenic compounds which are suitable as substrates for the detection and determination of enzymes having a hydrolytic action.

Chromogenic substrates for determining the activity of enzymes have been known for a long time. Thus, for example, benzoyl-arginyl-4-nitroanilide is used to determine quantitatively the trypsin action of an enzyme by a procedure in which the amount of 4-nitroaniline liberated per unit time is measured. This measurement is possible because the UV spectrum of the free 4-nitroaniline differs greatly from that of the N-acylated compound.

Similar substrates for determining the activity of serine proteases EC 3.421 are known, for example, from German Offenlegungsschriften Nos. 2,527,932, 2,552,570 and 2,629,067. Instead of the benzoyl radical, they contain N-protected peptides of 3-4 aminoacids. In this case also, the chromophoric group is usually 4-nitroaniline.

These substrates according to the state of the art have, however, deficiencies with regard to their specificity. Thus, for example, according to Thromb. Res. 10, 549 (1977), such substrates can be split not only by proteases but also by certain esterases, at almost the same rate. The object of the invention is, inter alia, to eliminate this deficiency.

The new compounds exhibit the disadvantage of unspecificity, when used as enzyme substrates according to the invention, to a far lesser extent than the substrates of the state of the art. Whilst a non-peptidic bond between a basic aminoacid and the chromogens is always split in the substrates according to the state of the art, in the peptides according to the invention there is a true peptide bond between the basic aminoacid and another naturally occurring aminoacid at the point at which they are split by the enzymes. In the case of enzymatic splitting, the new substrates therefore have properties closer to those of a protein than the compounds known hitherto. The sensitivity to esterases is greatly reduced by the insertion of one or more aminoacids between the splitting point and the chromophore whilst the specificity can be increased by varying these aminoacids. The invention relates, in particular, to the use of the new compounds as chromogenic or fluorescent substrates for the detection, and preferably for the quantitative determination, of proteolytic enzymes. The compounds can also be employed in a known manner in the determination of enzyme inhibitors. Above all, the compounds are suitable as chromogenic substrates in the determination of proteinases in body fluids of humans and animals.

The invention relates to compounds of the formula I

   (I)

wherein W denotes a hydrogen atom, an acyl group or a benzene- or toluene-sulfonyl group, P represents a radical of an aminoacid or of a di- to hexa-peptide, the side chain groups of which can be substituted, or represents a bond, B denotes arginine, lysine, phenylalanine, tyrosine or homoarginine, X denotes one or two radicals of L-aminoacids which occur in proteins and in which the side chain groups can be substituted, and R denotes an optionally substituted aromatic hydrocarbon radical, and wherein —X—NH—R represents a chromogenic or fluorogenic group and has the property of providing, under the hydrolytic action of an enzyme, a splitting product NH$_2$—R, the amount of which can be measured by photometric, spectrophotometric or fluorescencephotometric methods.

The preferred definitions are:

For W: an R$_1$—CO— group, wherein R$_1$ denotes an aliphatic hydrocarbon radical with 1-6 carbon atoms, an aromatic hydrocarbon radical with 6-10 carbon atoms, an araliphatic hydrocarbon radical with 7-10 carbon atoms or an alkaryl group with 6-10 carbon atoms, an R$_2$—O—CO— group, in which R$_2$ denotes an aliphatic hydrocarbon radical with 1-6 carbon atoms, an araliphatic hydrocarbon radical with 7-10 carbon atoms or an alkyl$_{1-6}$-sulfonylalkyl$_{2-6}$ group, a benzenesulfonyl group or an alkarylsulfonyl group with 7-10 carbon atoms;

For R: a nitrophenyl, naphthyl, nitronaphthyl, methoxynaphthyl, phenyl, methylnitrophenyl, dinitrophenyl, quinolyl or nitroquinolyl group or a salt thereof.

Particularly preferred definitions are:

For R: a nitrophenyl radical, which can be substituted by a halogen atom, a trifluoromethyl group, a carboxyl group, a methoxy group, a sulfonic acid group or a cyano group, a dimethoxycarbonylphenyl group, a pyridine radical, a nitrobenzothiazole radical or a pyrazine, triazole, benzopyrazole, chrysene, naphthyl, methoxynaphthyl, azulene or aminocoumarin radical, it being possible for the radicals to be substituted.

When the bond B—X in such a compound is split by the action of an enzyme to be detected or determined, a chromogenic aminoacid derivative H—X—NH—R is formed. In order to liberate the chromophore or fluorophore NH$_2$—R from this derivative, the bond X—N must be split, for which an enzyme with an aminopeptidase action is particularly suitable. The highest possible rate of splitting, good stability of the enzyme in solution and if possible lyophilisability are desired. A suitable enzyme with the abovementioned properties has been found, for example, in aminopeptidase K from the fungus *Tritirachium album Limber.*

The reaction sequence can thus be described as follows:

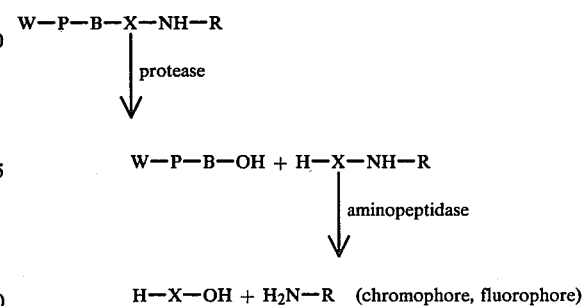

The reaction sequence described simultaneously shows the principle of the use of the compounds according to the invention in the determination of a proteinase: the proteinase splits the substrate at a specific bonding point, after which an aminopeptidase to be employed splits off the chromophore, which is available for a measuring process.

The invention relates, in particular, to the use of the compounds of the general formula I for the determination of hydrolytically active enzymes. This concerns a process for the determination of a hydrolytically active enzyme, which comprises adding a compound as claimed in any of claims 1 to 4 and an enzyme with an aminopeptidase action to the solution in which the enzyme is to be determined and, after an incubation period, measuring the product $NH_2R$ obtained from splitting the compound of the general formula I.

The chomophore or fluorophore split off is a direct measure of the activity of the hydrolytically active enzyme. The enzyme with an aminopeptidase action is an auxiliary enzyme in this process. Enzymes which have an aminopeptidase action and have been isolated from animal or human tissues or from microorganisms are particularly suitable here. Leucine aminopeptidase, aminopeptidase, aminopeptidase M or the abovementioned enzyme from *Tritirachium album limber* are examples of suitable enzymes in this context.

The compounds according to the invention can be characterized in more detail by the following representation by formula II:

$$W-A_1-A_2-A_3-A_4-A_5-A_6-B-X-NH-R \quad (II)$$

In this formula, $A_2$ to $A_6$ each denote a radical of an α-aminoacid or α-iminoacid and can be identical or different and substituted in their side chain groups, or denote a chemical bond. If th aminoacids are chiral aminoacids, they can be in the L-form or D-form. However, the aminoacids $A_2$ to $A_6$ are not restricted only to those which occur in proteins. α-Aminoacids such as, for example, α-aminoisobutyric acid (Aib), pipecolinic acid, azetidinecarboxylic acid, OMe-tyrosine, 1-aminocyclohexane-carboxylic acid, cysteic acid, phenylglycine (Phg), γ-benzimidazoyl-aminobutyric acid, spinacine and many others, as well as β-aminoacids, have also proved suitable for achieving a high enzyme specificity.

If the aminoacids $A_2$–$A_6$ additionally contain functional groups, such as OH, COOH, $NH_2$ or SH, these can be free or protected, examples of protected acids being protected arginine, histidine, asparagine or glutamine. An amino group in the side chain should always be acylated so that it provides no additional splitting points as a basic aminoacid. Possible protective groups are the radicals customary in peptide chemistry (compare E. Wünsch in Houben-Weyl, volume XV ½), for example esters or amides for carboxyl groups, preferably alkyl, aryl or aralkyl groups for hydroxyl and mercapto groups and simple alkanoyl or aroyl radicals, carbonic acid half-esters, toluenesulfonyl, trifluoroacetyl and others for amines.

Groups which are called protective groups in peptide chemistry as usually those chemical groups which can be split off under conditions under which the peptide bonds are not substantially changed. However, it is not necessary to split off such protective groups from the compounds according to the invention, for example the protective group W on the terminal N atom, in order to be able to use the compounds for the purpose according to the invention. The protective groups present in the peptide derivatives according to the invention therefore do not need to meet the condition of being able to be split off without damaging the remainder of the molecule. Possible protective groups in the context of the invention are therefore all those chemical groupings which are suitable for protecting the terminal amino group in the compounds according to the invention or protecting the side chain groups which are carried by the aminoacid radicals and are present in the parts of the molecule designated P and X, against an undesired chemical reaction during synthesis of these compounds, even if these chemical groupings cannot be split off from the compounds according to the invention without damaging the molecule. A protective group W on the terminal N atom or a protective group in the side chain of one of the aminoacids in the part of the molecule designated P or X can therefore be an acyl or sulfonyl group, preferably an $R_1$—CO— group, wherein $R_1$ denotes an aliphatic hydrocarbon radical which has 1-6 carbon atoms and can be substituted by 1-3 fluorine, chlorine, bromine or iodine atoms or carboxyl groups, an aromatic hydrocarbon radical which has 6-10 carbon atoms and can be substituted by 1-3 halogen atoms, an aliphatic hydrocarbon radical with 7-10 carbon atoms or an alkaryl group with 6-10 carbon atoms, or an $R_2O$—CO— group, in which $R_2$ denotes an aliphatic hydrocarbon radical with 1-6 carbon atoms, an araliphatic hydrocarbon radical with 7-10 carbon atoms or an $alkyl_{1-6}$-sulfonylalkyl$_{2-6}$ group, or a benzenesulfonyl group or an alkarylsulfonyl group with 7-10 carbon atoms, in particular including formyl (For), acetyl (Ac), benzoyl (Bz), trifluoroacetyl (TFA), benzyloxycarbonyl (Z), tert.-butoxycarbonyl (BOC), methoxycarbonyl (Meoc), ethoxycarbonyl (Etoc), methylsulfonylethoxycarbonyl (Msc), toluenesulfonyl (Tos), mesyl (Mes) or pyroglutamyl (pGlu), and furthermore a monoalkylated polyethylene glycol, the free OH group of which is linked to $A_1$ via an esteramide, urethane or urethane-ureide bond, succinyl (Suc) or maleyl (Mal).

The statements made in respect of the aminoacids $A_2$–$A_6$ initially apply to the aminoacid $A_1$. However, if W represents hydrogen, $A_1$ must be immune to attack by aminopeptidases or at least difficult to degrade. This applies, for example, to naturally occurring D-α-aminoacids or β-aminoacids, such as β-alanine, or other aminoacids, such as, for example, α-aminocaproic acid, pyroglutamic acid, glycine or serine, especially in conjunction with proline, pipecolinic acid or a D-aminoacid as $A_2$.

B is L-arginine, L-lysine, L-phenylalanine, L-tyrosine or L-homoarginine.

X denotes one or two radicals of aminoacids which occur naturally in proteins and in which the side chain groups can be substituted, preferably of an L-aminoacid with a hydrophobic side chain, for example phenylalanine, tyrosine, tryptophane, leucine and methionine, and hydrophobic derivatives of naturally occurring aminoacids, for example tertiary butyl-serine.

Numerous compounds can serve as the chromophore $H_2N$—R. The only prerequisite is that the free and acylated chromophore (bonded as —X—NH—R) have sufficiently different fluorescence or absorption spectra under the measuring conditions and that these spectra permit a clear quantitative determination of the free chromophore in the presence of the acylated chromophore. The compounds used in practice are known from the literature. Thus, in addition to simple 4-nitroaniline, which is most frequently used, examples of possible compounds are: 2- or 3-carboxy-4-nitroaniline, 2- or 3-halogeno-4-nitroaniline, 2-methoxy-4-nitro-5-methylaniline, sodium 4-nitroaniline-2-sulfonate, 2-nitro-4-trifluoromethylaniline, 2-nitro-4-cyanonitroaniline, 4-aminoazobenzene, 1-aminonaphthalene-4-sulfonic acid, 2-aminobenzimidazole, 2-aminopyrimidine, 4-aminopyridine, 1-aminotriazine, 3-aminoindazole, 5-nitro-2-aminobenzothiazole, methyl 3-aminoisophthalate, aminopyrene or aminocoumarins or derivatives thereof.

The compounds according to the invention are synthesised by the known methods of peptide chemistry. An example of an advantageous preparation procedure is the condensation of an aminoacid derivative or peptide derivative of the formula III $$W-A_{(1-6)}-OH \qquad (III)$$

wherein W and $A_1$ to $A_6$ have the abovementioned meaning, but wherein W does not denote a hydrogen atom and carboxyl and amino groups in the side chains of $A_1$–$A_6$ are substituted by protective groups, with a peptide of the formula IV $$H-B-X-NH-R \qquad (IV)$$

wherein B, R and X have the abovementioned meaning, but wherein amino and carboxyl groups in the side chains of the aminoacid radicals are substituted by protective groups. Other side chain groups can be substituted. If desired, the protective groups can subsequently be split off.

The condensation can be carried out by methods customary in peptide chemistry, for example by the azide method or by the method of mixed anhydrides. The convenient carbodiimide process is preferably used, optionally with the addition of a compound such as, for example, 1-hydroxybenzotriazole, as described in Chem. Ber. 103, 788 (1970). It is also possible to react active esters with the amine component. An example of a suitable solvent for the mixed anhydride process is tetrahydrofuran. Dimethylformamide, dimethylacetamide, dimethylsulfoxide or N-methylpyrrolidone are preferably used for the other methods.

A few chromogenic enzyme substrates which are characteristic of those described above are listed in Table 1 as examples of the large number of possible compounds according to the invention. All the compounds have been characterized by elementary analysis and aminoacid analysis. They represent a particular subject of the invention.

TABLE 1

| Chromogenic compounds |
|---|
| Z—Val—Arg—Val—pNa |
| pNa = p-nitroanilide |
| Boc—Ile—Glu(OBu$^t$)—Gly—Arg—Gly—pNa |
| Msc—Ile—Glu—Gly—Arg—Leu—pNa |
| Mes—Ile—Glu(OiPr)—Gly—Arg—Val—pNa |
| Tos—Ile—Glu(Morph)—Gly—Arg—Leu—pNa |
| Z—Val—Arg—Val—Phe—pNa |
| Etoc—Phe—Val—Arg—Phe—pNa |
| Meoc—Phg—Val—Arg—Phe—pNa |
| H—D-Phe—Val—Arg—Val—pNa |
| H—Gly—Pro—Gly—Gly—Arg—Leu—pNa |
| H—Gly—Pro—Glu—Gly—Arg—Leu—pNa |
| H—Gly—Pro—Lys(Ac)—Arg—Phe—pNa |
| H—β-Ala—Glu—Gly—Arg—Leu—pNa |
| Boc—D-Val—Leu—Lys—Leu—pNa |
| $CH_3$—PEG$_{600}$—CO—$(CH_2)_2$—CO—Val—Arg—Val—pNa |
| PEG$_{600}$ = polyethylene glycol 600 |
| Ac—Ile—Glu—Gly—Arg—Leu—pNa |
| Bz—Ile—Glu—Gly—Arg—Leu—pNa |
| Tos—Gly—Pro—Glu—Gly—Arg—Phe—pNa |
| H—Gly—Pro—Gly—Gly—Arg—Phe—pNa |
| H—Gly—Pro—Ala(SO$_3$Na)—Gly—Arg—Phe—pNa |
| Msc—Gly—Gly—Pro—Glu(OiPr)—Gly—Arg—Phe—pNa |
| $C_4H_9$—CO—Ala—Glu—Gly—Gly—Gly—Val—Arg—Tyr—pNa |
| Ac—Cys(But)—Glu—Gly—Gly—Gly—Val—Arg—Phe—pNa |
| pGlu—Ile—Glu—Gly—Arg—Leu—pNa |
| For—Ile—Glu—Gly—Arg—Phe—pNa |
| H—D-Lys(Boc)—Pro—Arg—Leu—pNa |
| Msc—Cys(Bzl)—Val—Arg—Phe—pNa |
| TFA—D-Phe—Pro—Arg—Phe—pNa |
| Mal—D-Phe—Pro—Arg—Phe—pNa |
| Suc—D-Phe—Pro—Arg—Phe—pNa |

A number of compounds of the general formula IV are listed in Table 2. They are suitable starting compounds for the synthesis of the substrates according to the invention and contain both the splitting point and the chromogen.

TABLE 2

Dipeptide-nitroanilide data

H—Arg—(X)—pNa.2Y

| X | Y | Melting point °C. (D = decomposition) | $(\alpha)_D^{22}$ C = 1 | Solvent | C | H | N (calculated (%)) | Halogen (%) |
|---|---|---|---|---|---|---|---|---|
| Gly | HCl | >134° (D) | +14.1° | MeOH | 40.1 (39.6) | 5.7 (5.5) | 22.8 (23.1) | 15.9 (16.7) |
| Ala | HCl | >86° (D) | −10.2° | MeOH | 41.2 (41.1) | 5.7 (5.7) | 22.1 (22.4) | 15.8 (16.2) |
| Val | HCl | >91° (D) | +6.8° | MeOH | 43.5 (43.8) | 6.2 (6.3) | 20.8 (21.0) | 14.9 (15.2) |
| Leu | HCl | >115° (D) | +13.3° | MeOH | 44.7 (45.0) | 6.5 (6.5) | 19.9 (20.4) | 14.3 (14.8) |
| Phe | HBr | >99° (D) | +59.4° | MeOH | 41.5 (41.8) | 4.7 (4.8) | 16.2 (16.3) | 26.3 (26.5) |
| Tyr | HCl | >120° (D) | +77.8° | MeOH | 45.3 (45.1) | 6.3 (6.4) | 13.3 (13.1) | 15.9 (16.6) |

H—Lys—(Msc)—(X)—pNa.Y

| X | Y | Melting point °C. (D = decomposition) | $(\alpha)_D^{22}$ C = 1 | Solvent | C | H | N | S (calculated (%)) | Halogen (%) |
|---|---|---|---|---|---|---|---|---|---|
| Gly | HBr | 225–228° (D) | +14.6° | MeOH | 38.8 (39.0) | 5.2 (5.1) | 12.3 (12.6) | 5.7 (5.8) | 14.6 (14.4) |
| Leu | HBr | >93° (D) | −1.5° | MeOH | 42.4 (42.3) | 5.9 (5.9) | 11.3 (11.5) | 5.2 (5.3) | 13.4 (13.1) |
| Phe | HBr | >117° (D) | +65.7° | MeOH | 46.3 (46.6) | 5.2 (5.3) | 11.0 (10.9) | 4.9 (5.0) | 12.6 (12.4) |

TABLE 2-continued

| | | | Dipeptide-nitroanilide data | | | | |
|---|---|---|---|---|---|---|---|
| Tyr | HBr | >132° (D) | +61.8° MeOH | 45.7 (45.5) | 5.1 (5.2) | 10.9 (10.6) | 5.0 (4.9) | 12.0 (12.1) |

Table 3 lists some compounds according to the invention in which the chromogenic radical has been varied, the component W—A—B—X—NH being kept constant. This is not a complete list of all the conceivable radicals, but only a few examples which are intended to illustrate the invention in this respect.

TABLE 3

Chromogenic compounds of the formula
Z—Val—Arg—Val—NH—R

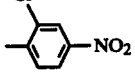

TABLE 3-continued

Chromogenic compounds of the formula
Z—Val—Arg—Val—NH—R

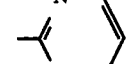

The rates at which some compounds according to the invention are split by various proteolytic enzymes are compared with one another in Table 4. The figures give the time in minutes which is required to obtain an increase of 0.1 unit (U) in the optical density (OD) of 1.5 molar solution of the substrate, at 405 nm, by the enzymes indicated.

The splitting rates are in most cases reduced by the increased bond energy of the true peptide bonds compared with the nitroanilide bond. In addition to the specificity, the splitting rate can also be influenced by varying X. Because the splitting rate can be adjusted more easily (by varying X), it is frequently also possible to use a higher enzyme concentration; repeated dilution is therefore eliminated as an additional source of error in enzyme determinations.

TABLE 4

Comparison of the rates at which various substrates are split by proteolytic enzymes (the figures give the time in minutes required to achieve an increase in extinction of 0.1 U of optical density (OD) at 405 nm)

| Substrates 1.5 m moles/l | Thrombin 6 IU/ml | Plasmin 2 CTA-U/ml | F Xa 0.2 U/ml | Kallikrein 0.85 BAEE-U/ml | F XIIa 3.6 U/ml |
|---|---|---|---|---|---|
| Substrates for thrombin, according to the state of the art: | | | | | |
| H—D-Phe—Pip—Arg↓PNa | 0.4 | 2.0 | 6.3 | 0.5 | 0.3 |
| Tos—Gly—Pro—Arg↓pNa | 0.3 | 0.4 | 0.7 | 0.4 | 0.2 |
| Substrates for thrombin, according to the invention: | | | | | |
| H—D-Phe—Pro—Arg↓Leu—pNa | 1.3 | 33.0 | 94.0 | 4.7 | 2.5 |
| H—D-Phe—Pro—Arg↓Val—pNa | 5.3 | — | — | 1.6 | 10.9 |

TABLE 4-continued

Comparison of the rates at which various substrates are split by proteolytic enzymes (the figures give the time in minutes required to achieve an increase in extinction of 0.1 U of optical density (OD) at 405 nm)

| Substrates 1.5 m moles/l | Thrombin 6 IU/ml | Plasmin 2 CTA-U/ml | F Xa 0.2 U/ml | Kallikrein 0.85 BAEE-U/ml | F XIIa 3.6 U/ml |
|---|---|---|---|---|---|
| Substrates for kallikrein, according to the state of the art: | | | | | |
| Bz—Pro—Phe—Arg↓pNa | — | 3.4 | — | 0.2 | 12.8 |
| H—D-Pro—Phe—Arg↓pNa | 6.9 | 0.4 | 3.5 | 0.11 | 0.5 |
| Substrates for kallikrein, according to the invention: | | | | | |
| MSC—Val—Arg↓Val—pNa | — | — | — | 1.8 | — |
| Z—Val—Arg↓Val—pNa | — | — | — | 1.4 | — |
| Z—Val—Arg↓Phe—pNa Boc—Gly—Pro—Glu (O—But)— | — | — | — | 3.8 | — |
| Gly—Arg↓Phe—pNa Boc—Ile—Glu (O—But) Gly— | — | — | — | 0.91 | — |
| Arg↓Leu—pNa | — | — | 36.0 | 1.6 | — |
| Boc—Gly—Pro—Leu—Gly—Arg↓Leu—pNa | — | — | — | 0.5 | — |
| Boc—D-Val—Glu (O—But) Gly≤ Arg↓Leu—pNa | — | — | 5.6 | 1.4 | — |
| Bz—Ile—Glu—Gly—Arg↓Phe—pNa | — | — | — | 4.7 | — |
| H—D-Phe—Glu—Gly—Arg↓Phe—pNa | — | — | — | 2.0 | — |
| H—D-Glu—Gly—Arg↓Leu—pNa | — | — | — | 2.7 | — |
| H—D-Ala—Glu—Gly—Arg↓Leu—pNa | — | — | — | 3.4 | — |
| Substrates for plasmin, according to the state of the art: | | | | | |
| H—D-Val—Leu—Lys↓pNa— | — | 0.4 | — | 0.5 | — |
| Substrates for plasmin, according to the invention: | | | | | |
| Boc—D-Val—Leu—Lys↓Leu—pNa | — | 3.3 | — | 15.0 | — |

↓ point at which the substrates indicated are split by serine proteases
— no detectable splitting of the substrate Table 5 contains some examples of the change achieved in the specificity of substrates by varying X. It is found that the introduction of the group X provides a large number of new possibilities for influencing the specificity.

In Table 6, the quotients of the rates at which substrates according to the state of the art and substrates according to the invention are split by thrombin and acetylated thrombin in accordance with the instructions of Landaburu and Seegers, Can. J. Biochem. Physiol. 37, 1361 (1959), are compared. Thrombin acetylated in this manner no longer has a clotting activity, but has an esterase activity similar to that before acetylation. Compared with an activated acid amide bond in the substrates according to the state of the art, the splitting of a true peptide bond in the substrates according to the invention permits a better differentiation between native proteases and partially changed proteases which have lost their proteolytic activity but still have an esterolytic action, and leads to a considerable gain in specificity.

The danger of misinterpretations of the results of protease determinations using these substrates is considerably less than has been described by Gaffney et al. in Thromb. Res. 10, 549 (1977) for chromogenic substrates known hitherto.

TABLE 5

Change in the specificity of the protease substrates by replacement of the aminoacid at the variable point X in formula 1 (the figures indicate the time in minutes which is required to achieve an increase in extinction of 0.1 U of optical density (OD) at 405 nm)

| Substrates 1.5 m moles/l | Thrombin 6 IU/ml | Plasmin 2 CTA-U/ml | F Xa 0.2 U/ml | Kallikrein 0.85 BAEE-U/ml | F XIIa 3.6 U/ml |
|---|---|---|---|---|---|
| P—B—X—NH—R | | | | | |
| H—D-Phe—Pro—Arg↓Leu—pNa | 1.3 | 33.3 | 94.0 | 4.7 | 2.5 |
| H—D-Phe—Pro—Arg↓Phe—pNa | 0.6 | 9.6 | 2.1 | 5.6 | 2.9 |
| H—D-Phe—Pro—Arg↓Tyr—pNa | 0.8 | 7.1 | 2.5 | 2.0 | 2.1 |
| H—D-Phe—Pro—Arg↓Ser—pNa | — | — | — | — | — |
| Boc—D-Val—Glu(O—But)—Gly—Arg↓Gly—pNa | — | — | — | — | — |
| Boc—D.Val—Glu(O—But)—Gly—Arg↓Leu—pNa | — | — | — | 1.4 | — |
| Z—Arg↓Ser(O—But)—pNa | — | — | — | 4.8 | — |
| Z—Arg↓Val—pNa | — | — | — | 11.1 | — |
| Z—Arg↓Gly—pNa | — | — | — | — | — |
| H—D-Val—Glu—Gly—Arg↓Leu—pNa | — | — | — | 5.9 | — |
| H—D-Val—Glu—Gly—Arg↓Ser—pNa | — | — | — | — | — |
| H—D-Val—Glu—Gly—Arg↓Gly—pNa | — | — | — | — | — |
| Boc—D-Val—Leu—Lys↓Tyr—pNa | — | 1.4 | — | 12.5 | — |
| Boc—D-Val—Leu—Lys↓Leu—pNa | — | 3.3 | — | 15.0 | — |
| Boc—D-Val—Leu—Lys↓Phe—pNa | — | 3.3 | — | — | — |
| Boc—D-Val—Leu—Lys↓Gly—pNa | — | — | — | — | — |

↓ = point at which the substrates indicated are split by serine proteases
— = no measurable splitting of the substrate

TABLE 6

Quotients of the rates at which chromogenic substrates are split before and after acetylation, with the aid of 2 thrombin batches

| Substrate | Batch 1 Q* | Batch 2 Q* |
|---|---|---|
| Substrates according to the state of the art: | | |
| Tos—Gly—Pro—Arg↓pNa | 2.2 | 2.4 |
| Bz—Phe—Val—Arg↓pNa | 3.1 | 2.5 |
| H—D-Phe—Pip—Arg↓pNa | 1.4 | 1.3 |
| Substrates according to the invention: | | |
| H—D-Phe—Pro—Arg↓Leu—pNa | 7.0 | 5.6 |
| Boc—D-Phe—Pro—Arg↓Tyr—pNa | 10.3 | 10.6 |
| Meoc—D-Phe—Pro—Arg↓Leu—pNa | 9.0 | 6.8 |

*Q = $\frac{\text{milli-Units/mg of protein, before acetylation}}{\text{milli-Units/mg of protein, after acetylation}}$ ↓ = point at which the chromogenic substrates are split by serine proteases/esterases The following examples illustrate first the preparation of the new compounds and then their use for the determination of proteolytic enzymes.

EXAMPLE 1

Z-Val-Arg-Val-pNa 1.1. Z-Val-pNa 25.1 g (0.1 mole) of Z-Val-OH, 13.8 g (0.1 mole) of p-nitroaniline and 13.6 g (0.2 mole) of imidazole are dissolved in 120 ml of tetrahydrofuran, the solution is cooled to −20° C. and 9.3 ml (0.1 mole) of phosphorus oxytrichloride are added. The reaction mixture is stirred at room temperature for 24 hours and then poured onto ice-water and rendered alkaline with sodium carbonate. The aqueous solution is extracted several times with ethyl acetate and the organic phase is dried over sodium sulfate and evaporated. The residue is recrystallized from hot alcohol using active charcoal.

Yield: 18.9 g (51%).

Melting point: 192°–194° C.; $(\alpha)_D^{22}$: −16.4° (c=1, methanol).

Elementary analysis: (371.38) $C_{19}H_{21}N_3O_5$: C, 61.3 (61.44); H, 5.55 (5.70); N, 11.2 (11.31).

1.2. H-Val-pNa-HBr 11.8 g (32 mmoles) of Z-Val-pNa are suspended in 150 ml of glacial acetic acid, 37.5 ml of 40% strength HBr/glacial acetic acid are added and the solution is stirred at room temperature for 1 hour. The reaction batch is then poured into 1.5 l of ether and the precipitate obtained is filtered off, washed thoroughly with dry ether and dried over KOH in vacuo.

Yield: 7.7 g.

Melting point: 130° C. (decomposition); $(\alpha)_D^{22}$: +52.7° (c=1, methanol).

Elementary analysis: (318.18) $C_{11}H_{16}BrN_3O_3$: C, 41.4 (41.62); H, 5.0 (5.06); Br, 24.9 (25.11); N, 13.1 (13.2).

1.3. H-Arg-Val-pNa. 2 HCl 7.3 g (23 mmoles) of H-Val-pNa.HBr, 7.1 g (23 mmoles) of Boc-Arg-OH.HCl and 3.1 g (23 mmoles) of HOBt are dissolved in 70 ml of dimethylformamide, the solution is cooled to 0° C. and 4.7 g (23 mmoles) of dicyclohexylcarbodiimide are added. The mixture is neutralized with 8.7 ml of N-ethylmorpholine and is stirred at room temperature for 16 hours. The reaction mixture is freed from the dicyclohexylurea which has precipitated, the clear solution is evaporated. The residue is partitioned between NaHCO₃ solution and N-butanol and the butanol phase is evaporated to dryness. The residue is chromatographed over silica gel using a mobile phase of $CHCl_3/CH_3OH/H_2O/HCOOH$ (400/100/10/3; v/v). The pure dipeptide fraction is collected and evaporated to dryness and the residue is triturated with ether, filtered off and dried in vacuo over $P_2O_5$. A 50% strength aqueous-methanolic solution of the substance is treated with the ion exchanger Amberlite IRA-410 (Cl-form) and thus converted into the hydrochloride.

Yield: 9.3 g ( ≙ 76%).

The substance thus obtained is now dissolved in 100 ml of 1.2 N HCl in glacial acetic acid and the solution is stirred at room temperature for 1 hour. After evaporating off the solvent, the residue is digested with ether, the mixture is filtered and the product phase is washed with ether and dried over KOH in vacuo.

Yield: 7.8 g (95.5%).

Melting point: >91° C. (decomposition); $(\alpha)_D^{23}$: +6.8° (c=1, methanol).

1.4. Z-Val-Arg-Val-pNa.HCl 7.8 g (16.7 mmoles) of H-Arg-Val-pNa.2 HCl, 8.6 g (20 mmoles) of Z-Val-OTc and 2.7 g (20 mmoles) of HOBt are dissolved in 75 ml of dimethylformamide, and 6.5 ml of N-ethylmorpholine are added. After a reaction time of 16 hours the solvent is evaporated off and the residue which remains is digested several times with petroleum ether, after which the petroleum ether extract is discarded. The product is now partitioned between NaHCO₃ solution and n-butanol, the butanol phase is evaporated and the substance thus obtained is chromatographed over silica gel using a mobile phase of $CHCl_3/CH_3OH/H_2O/HCOOH$ (400/100/10/1; v/v). The pure tripeptide fraction is collected and evaporated to dryness and the residue is digested with ether, filtered off and dried over $P_2O_5$.

Yield: 7.0 g (63%).

Melting point: 152° C. (decomposition); $(\alpha)_D^{22}$: −51.5° (c=1, methanol).

Elementary analysis: (663.17) $C_{30}H_{43}ClN_8O_7$: C, 54.0 (54.33); H, 6.5 (6.54); N, 16.8 (16.89); Cl, 5.2 (5.38).

The compound is suitable as a substrate for the determination of kallikrein from human plasma.

EXAMPLE 2

Boc-Gly-Pro-Glu(O-But)-Gly-Arg-Phe-pNa

2.1 Z-Phe-pNa 29.9 g (0.1 mole) of Z-Phe-OH, 13.8 g (0.1 mole) of nitroaniline and 13.6 g (0.2 mole) of imidazole are dissolved in 150 ml of tetrahydrofuran and are reacted with POCl₃ in a manner analogous to that in 1.1.

Yield: 29.6 g (70.5%).

Melting point: 132° C. (decomposition); $(\alpha)_D^{22}$: +55.6° (c=1, methanol/dimethylformamide 1:1).

2.2 H-Phe-pNa.HBr 15 g (35.8 mmoles) of Z-Phe-pNa are suspended in 100 ml of glacial acetic acid, 80 ml of 36% strength HBr in glacial acetic acid are added and the mixture is stirred at room temperature for 1 hour. It is then poured into 1.5 l of dry ether and the precipitate is filtered off, washed with ether and dried over KOH in vacuo.

Yield: 12.3 g (93.8%).

Melting point: 126°–128° C.; $(\alpha)_D^{22}$: +77.7° (c=1, dimethylformamide).

2.3. H-Arg-Phe-pNa.2 HBr 18.3 g (50 mmoles) of H-Phe-pNa.Br, 15.5 g (50 mmoles) of Boc-Arg-OH.HCl and 6.75 g (50 mmoles) of HOBt are dissolved in 150 ml of dimethylformamide, the solution is cooled to 0° C. and 10.3 g (50 mmoles) of dicyclohexylcarbodiimide and 13.9 ml of N-ethylmorpholine are added. After a reaction time of 16 hours, the precipitate which has separated out is filtered off and the filtrate is evaporated to dryness. The residue is partitioned between NaHCO₃ solution and ethyl acetate, the ethyl acetate extract is evaporated, the residue is dissolved in tetrahydrofuran and the product is precipitated with ether.

Yield: 27.7 g (95%).

The substance is converted into the hydrochloride with the ion exchanger Amberlite IRA 410 (Cl-form).

$(\alpha)_D^{22}$: +10.8° (c=1, methanol).

13.5 g (23.3 mmoles) of Boc-Arg-Phe-pNa.HCl are stirred in 100 ml of 1N HCl in glacial acetic acid at room temperature for 1 hour, the mixture is concentrated and a solid is precipitated with ether and filtered off. The solid is dissolved in a little methanol and the solution is stirred with 5 g of pyridine hydrobromide. After adding ether, the precipitate formed is filtered off, washed thoroughly with ether and dried over KOH in vacuo.

Yield: 12.4 g (=88%).

Melting point: 99° C. (decomposition); $(\alpha)_D^{22}$: +59.4° (c=1, methanol).

2.4 Boc-Gly-Pro-OH 27.6 g (78 moles) of Boc-Gly-OTcp and 8.95 g (78 mmoles) of proline are dissolved in 200 ml of dimethylformamide. 10 ml (78 mmoles) of N-methylmorpholine are added and the mixture is kept at room temperature overnight. The solvent is then distilled off in vacuo and the residue is partitioned between 100 ml of n-butanol and 50 ml of 10% strength $KHSO_4/K_2SO_4$ (1:1), the aqueous phase is extracted twice with 50 ml of n-butanol each time, the combined butanol phases are washed with 20 ml of 10% strength NaCl solution and the butanol is distilled off in vacuo. The residue is dissolved in 50 ml of ethyl acetate. A small amount of salts is filtered off, the ethyl acetate solution is concentrated to half and 17.5 g (82.5%) of the chromatographically pure peptide are precipitated with 100 ml of petroleum ether.

2.5 Z-Glu(O-But)-Gly-OMe 33.8 g (0.1 mole) of Z-Glu(O-But)-OH, 12.6 g (0.1 mole) of H-Gly-OMe.HCl, 13.5 g (0.1 mole) of 1-hydroxybenzotriazole and 26 ml (0.2 mole) of N-ethylmorpholine are dissolved in 300 ml of dimethylformamide. 22 g (106 mmoles) of dicyclohexylcarbodiimide are added and the mixture is stirred overnight at room temperature. After filtering off the dicyclohexylurea, the solvent is distilled off in vacuo. The residue is dissolved in 100 ml of ethyl acetate and the solution is filtered. The filtrate is extracted by shaking with saturated bicarbonate solution and 10% strength citric acid and the ethyl acetate solution is washed with a little water and dried over sodium sulfate and the solvent is distilled off in vacuo. A resin, which slowly crystallizes completely, remains.

Yield of almost chromatographically pure compound: 37.1 g (91%).

2.6 H-Glu(O-But)-Gly-OMe. TosOH 13.2 g of the Z-compound are catalytically hydrogenated on Pd in 100 ml of methanol, with filtration with 1N methanolic TosOH. After 30 minutes, the reaction has ended. The catalyst is filtered off and the methanol is distilled off in vacuo. The residue is dried using an oil pump.

Yield: 13.0 g of oil (91.5%): almost chromatographically pure.

2.7. Boc-Gly-Pro-Glu(O-But)-Gly-OMe 2.7 g (10 mmoles) of Boc-Gly-Pro-OH and 4.5 g (10 mmoles) of H-Glu(O-But)-Gly-OMe.TosOH are dissolved in 20 ml of dimethylformamide. 1.28 ml (10 mmoles) of N-ethylmorpholine and 2.2 g (10.6 mmoles) of dicyclohexylcarbodiimide are added and the mixture is left to stand at room temperature overnight. The dicyclohexylurea is then filtered off, the solvent is distilled off in vacuo, the residue is taken up in ethyl acetate and the solution is washed with citric acid, bicarbonate solution and water, as described above, dried over sodium sulfate and evaporated to dryness. The residue is dissolved in ether and a precipitate is obtained with petroleum ether and filtered off.

Yield: 2.9 g (55%) of chromatographically pure compound.

2.8. Boc-Gly-Pro-Glu(O-But)-Gly-OH 2.2 g (4.2 mmoles) of the methyl ester are dissolved in a mixture of 15 ml of dioxan, 5 ml of methanol and 7 ml of water. The ester is saponified at pH 12.5 using an autotitrator. After 4.6 ml of 1N NaOH have been consumed, the reaction has ended. The mixture is neutralized with 1N HCl, the solvent is distilled off, the residue is diluted with water and the remainder of the 1N HCl is added until the equivalence point is reached. The turbid aqueous solution is extracted three times with ethyl acetate and the combined ethyl acetate solutions are washed with a little water, dried over sodium sulfate and concentrated to dryness in vacuo. The product is precipitated from ether/petroleum ether.

Yield: 1.88 g (89%) of the chromatographically pure compound. $(\alpha)_D^{22}$: $-65.2°$ (c=1, in methanol).

C.H.N: correct.

2.9. Boc-Gly-Pro-Glu(O-But)-Gly-Arg-Phe-pNa.HBr 514 mg (1 mmole) of Boc-Gly-Pro-Glu(O-But)-Gly-OH. 603.5 mg (1 mmole) of H-Arg-Phe-pNa.2 HBr and 135 mg (1 mmole) of HOBt are dissolved in 2 ml of dimethylformamide at 0° C. and 206 mg (1 mmole) of dicyclohexylcarbodiimide and 0.38 ml of N-ethylmorpholine are added. The solution is stirred at room temperature for 16 hours, the precipitate which has separated out is filtered off, the filtrate is evaporated to dryness and the residue is partitioned between ethyl acetate and NaHCO3 solution. The ethyl acetate phase is dried over Na2SO4 and evaporated, the residue is dissolved in a little methanol and the product is precipitated with ether. Finally, the solid is chromatographed over silica gel using a mobile phase of CHCl3/CH3OH/H2O/CH3COOH (200/100/15/10; v/v). The pure hexapeptide-anilide fraction is collected and evaporated, the residue is dissolved in a little methanol, 50 mg of pyridine hydrobromide are added to this solution and the product is precipitated by adding ether dropwise to the vigorously stirred solution and is centrifuged off.

Yield: 146 mg; $(\alpha)_D^{22}$: $-22.7°$ (c=1, methanol).

Aminoacid composition: Glu: 0.93; Pro: 0.8; Gly: 1.95; Phe: 0.96; and Arg: 1.0.

The compound is suitable as a substrate for the determination of kallikrein from human plasma.

EXAMPLE 3

Meoc-Ile-Glu-(O-But)-Gly-Arg-Phe-pNa 3.1. Meoc-Ile-OH 26.2 g (0.2 mole) of isoleucine are dissolved in 100 ml of 2N NaOH and 80 ml of water. 17 ml (0.22 mole) of methyl chloroformate and 116 ml of 2N NaOH are simultaneously added dropwise at 0° C., whilst mixing with a vibromixer. 1 hour after the addition has ended, the mixture is extracted with ether and the aqueous solution is brought to pH 2 with concentrated HCl and extracted again with ether. The ether solution is washed with a little 1N HCl and with water, dried over sodium sulfate and evaporated to dryness. The residue is taken up in a little ether and 31.2 g of Meoc-Ile-OH (82%) are precipitated with petroleum ether.

Melting point: 73° C.; $(\alpha)_D^{22}$: $-3.0°$ (c=1, in methanol).

3.2. Meoc-Ile-Glu(O-But)-Gly-OMe 1.89 g (10 mmoles) of Meoc-Ile-OH and 4.5 g (10 mmoles) of H-Glu(O-But)-Gly-OMe.TosOH are dissolved in 20 ml of dimethylformamide. 1.28 ml (10 mmoles) of N-ethylmorpholine and 2.2 g (10.6 mmoles) of dicyclohexylcarbodiimide are added and the mixture is stirred overnight. After filtration, the solvent is distilled off in vacuo, the residue is taken up in ethyl acetate and the ethyl acetate solution is washed with citric acid, sodium bicarbonate solution and water, as described above, and dried over sodium sulfate and evaporated. The residue is digested with a little ice-cold ethyl acetate and ether.

Yield: 3.15 g (70.8%).

Melting point: 155°–156° C.

$(\alpha)_D^{22}$: $-42.8°$ (c=1, in methanol). C,H,N: correct.

3.3. Meoc-Ile-Glu(O-But)-Gly-OH 2.9 g (5.9 mmoles) of the above ester in 30 ml of dioxan/methanol/water (30:20:5) are saponified with 6.9 ml of 1N NaOH at pH 12.5 (using an autotitrator). The mixture is then adjusted to a neutral pH value with 1.8 ml of 1N HCl and is concentrated in vacuo, 5.1 ml of 1N HCl are added to the residue and the mixture is extracted with ethyl acetate. The ethyl acetate solution is washed with a little water, dried over sodium sulfate and concentrated. The oil which remains solidifies with ether.

Yield: 1.95 g (76%).

Melting point: 110° C.; $(\alpha)_D^{22}$: $-44.7°$ (c=1, in methanol).

C,H,N: correct.

3.4. Meoc-Ile-Glu(O-But)-Gly-Arg-Phe-pNa.HCl 648 mg (1.5 mmoles) of Meoc-Ile-Glu(O-But)-Gly-OH. 905 mg (1.5 mmoles) of H-Arg-Phe-pNa.2HBr and 205 mg (1.5 mmoles) of HOBt are dissolved in 4.5 ml of dimethylformamide and the solution is cooled to 0° C.

309 mg (1.5 mmoles) of dicyclohexylcarbodiimide and 0.57 ml of N-ethylmorpholine are added to this mixture. After a reaction time of 16 hours, the precipitate which has separated out is filtered off, the solvent is evaporated off and the oil which remains is triturated with ether, whereupon a solid is formed. This is filtered off, washed thoroughly with ether and purified by chromatographing twice using LH 20/methanol.

Yield: 575 mg.

$(\alpha)_D^{22}$: −11.2° (c=1, methanol).

The compound is suitable as a substrate for the determination of the clotting factor X.

EXAMPLE 4

H-D-Phe-Pro-Arg-Phe-pNa 4.1. Boc-D-Phe-Pro-Bzl 13.43 g (55.5 mmoles) of H-Pro-OBzl.HCl and 7.5 g (55.5 mmoles) of HOBt are dissolved in 70 ml of dimethylformamide, the solution is cooled to 0° C. and 7.1 ml of N-ethylmorpholine and 12.1 g (58.7 mmoles) of dicyclohexylcarbodiimide are added. The reaction mixture is stirred at 0° C. for 3 hours and at room temperature for 4 hours, the precipitate is filtered off and the filtrate is evaporated to dryness. The residue is taken up in ethyl acetate/ether (2:1; v/v) and the mixture is extracted by shaking with in each case three portions of citric acid solution, NaHCO$_3$ solution and NaCl solution, the organic phase is dried over Na$_2$SO$_4$ and concentrated and the residue is separated by chromatography over silica gel using a mobile phase of CHCl$_3$/CH$_3$OH (50/1, v/v). The pure dipeptide fraction is collected and evaporated. An oily substance which is pure according to thin layer chromatography remains.

Yield: 19 g ( ≙ 75%).

4.2. Boc-D-Phe-Pro-OH 19 g (41.9 mmoles) of Boc-D-Phe-Pro-OBzl are dissolved in 400 ml of methanol and are hydrogenated in the presence of Pd/active charcoal in the course of 4 hours. The catalyst is separated off by filtration over kieselguhr, the filtrate is concentrated and the product is precipitated with petroleum ether.

Yield: 14.2 g (93%).

Melting point: 168°–171° C.; $(\alpha)_D^{22}$: −90.8° (c=1, methanol).

4.3. H-D-Phe-Pro-Arg-Phe-pNa.CF$_3$COOH 370.4 mg (1.02 mmoles) of Boc-D-Phe-Pro-OH, 615.4 mg (1.02 mmoles) of H-Arg-Phe-pNa.HBr and 137.9 mg (1.02 mmoles) of HOBt are dissolved in 3 ml of dimethylformamide, the solution is cooled to 0° C. and 230 mg (1.12 mmoles) of dicyclohexylcarbodiimide are added. After adding 0.13 ml of N-ethylmorpholine, the mixture is stirred at 0° C. for 1 hour and for a further 8 hours at room temperature, the precipitate is filtered off and the filtrate is evaporated to dryness. The residue is partitioned between NaHCO$_3$ solution and n-butanol, the butanol phase is dried with K$_2$CO$_3$ and concentrated and the product is precipitated with ether.

Yield: 504 mg ( ≙ 54%); $(\alpha)_D^{22}$: −32.3° (c=1, methanol).

Melting point: 160° C.

450 mg (0.44 mmole) of Boc-D-Phe-Pro-Arg-Phe-pNa.HBr are dissolved in 4 ml of trifluoroacetic acid, with the addition of 0.1 ml of anisole, and the solution is stirred at room temperature for 45 minutes. The product is precipitated with ether, centrifuged off and triturated with ether and centrifuged off again several times. The dried substance is triturated with NaHCO$_3$ solution, the mixture is extracted with n-butanol, the organic phase is dried with K$_2$CO$_3$ and filtered and the filtrate is evaporated to dryness. The solid residue is triturated with ether and centrifuged off.

Yield: 320 mg.

Melting point: 156°–158° C.

The compound is suitable as a substrate for the determination of thrombin and thrombin inhibitors.

EXAMPLE 5

Boc-D-Val-Leu-Lys-Leu-pNa 5.1. Z-Lys(Msc)-Leu-pNa 4 g (10 mmoles) of Z-Lys(Msc)-OH, 3.3 g (10 mmoles) of H-Leu-pNa.HBr and 1.35 g (10 mmoles) of HOBt are dissolved in 45 ml of dimethylformamide at 0° C. and 2.06 g (10 mmoles) of dicyclohexylcarbodiimide and 2.5 ml of N-ethylmorpholine are added. After a reaction time of 20 hours at room temperature, the precipitate which has separated out is filtered off, the filtrate is concentrated, the oil which remains is taken up in ethyl acetate and the mixture is extracted by shaking with three portions of phosphate buffer (pH 7), two portions of KHSO$_4$ solution and two portions of water. The ethyl acetate phase is dried over Na$_2$SO$_4$ and evaporated and the residue is triturated with ether, filtered off and recrystallized from ethyl acetate.

Yield: 4.85 g (76%).

Melting point: 159°–161° C. (decomposition): $(\alpha)_D^{22}$: 7.4° (c=1, dimethylformamide).

C,H,N,S: correct.

5.2. H-Lys(Msc)-Leu-pNa.HBr 4 g (6.2 mmoles) of Z-Lys(Msc)-Leu-pNa are dissolved in 20 ml of ethyl acetate and 12 ml of glacial acetic acid and the solution is stirred with 8 ml of 36% strength HBr in glacial acetic acid, first at 0° C. for 1 hour and then at room temperature for 1 hour. The mixture is then concentrated, the residue is digested with ether and the solid is filtered off, washed thoroughly with ether and dried over KOH in vacuo.

Yield: 2.5 g (67%).

Melting point: 225°–228° C.; $(\alpha)_D^{22}$: +14.6° (c=1, methanol).

5.3. Boc-D-Val-Leu-OH 10.86 g (50 mmoles) of Boc-D-Val-OH, 9.08 g (50 mmoles) of H-Leu-OMe.HCl and 6.75 g (50 mmoles) of HOBt are dissolved in 200 ml of dimethylformamide. The solution is cooled to 0° C. and 10.3 g (50 mmoles) of dicyclohexylcarbodiimide and 12.5 ml of N-ethylmorpholine are added. The solution is stirred at room temperature for 20 hours, the precipitate is then filtered off and the filtrate is evaporated to dryness. The oil which remains crystallizes when treated with ether and petroleum ether.

Yield: 11.5 g (66.7%).

Melting point: 86°–88° C.; $(\alpha)_D^{22}$: −15.4° (c=1, dimethylformamide).

11.4 g (33 mmoles) of Boc-D-Val-Leu-OMe are dissolved in 80 ml of dioxan and 10 ml of water, the calculated amount of 1N NaOH is added in portions and the mixture is stirred at room temperature for 2 hours. It is then acidified with KHSO$_4$, covered with a layer of 300 ml of ethyl acetate and extracted by shaking. The ethyl acetate phase is dried over Na$_2$SO$_4$ and concentrated and the product is crystallized with the addition of petroleum ether.

Yield: 10.3 ( ≙ 94%).

Melting point: 144°-146° C.; $(\alpha)_D^{22}$: −9.8° (c=1, dimethylformamide).

5.4. Boc-D-Val-Leu-Lys(Msc)-Leu-pNa 0.68 g (3.3 mmoles) of dicyclohexylcarbodiimide and 0.8 ml of N-ethylmorpholine are added to 1.93 g (3.3 mmoles) of H-Lys(Msc)-Leu-pNa.HBr, 1.09 g (3.3 mmoles) of Boc-D-Val-Leu-OH and 0.45 g (3.3 mmoles) of HOBt in 10 ml of dimethylformamide at 0° C. and the mixture is stirred at room temperature for 16 hours. After filtering off the dicyclohexylurea, the filtrate is evaporated, the residue is taken up in ethyl acetate/n-butanol (1/1; v/v) and the mixture is extracted by shaking successively with pH 7 buffer, water, $KHSO_4$ solution and water and is dried over $Na_2SO_4$. The solvent is evaporated off and the residue is triturated with ether, filtered off, washed with ether and dried in vacuo over $P_2O_5$.

Yield: 2.2 g ( $\triangle$ 79%).

Melting point: 188°-190° C. (decomposition); $(\alpha)_D^{22}$: −7.2° (c=1, dimethylformamide).

5.5 Boc-D-Val-Leu-Lys-Leu-pNa.HCl 1.6 g (1.9 mmoles) of Boc-D-Val-Leu-Lys(Msc)-Leu-pNa are dissolved in 40 ml of methanol, the solution is cooled to 0° C., 40 ml of NaOH (2N) are added and, after 5 minutes, the mixture is neutralized with the same amount of hydrochloric acid. The solution is evaporated to dryness, the residue is extracted with methanol and the methanol extract is chromatographed over LH 20 using methanol as the mobile phase. The pure tetrapeptide fraction is collected and evaporated and the residue is triturated with ether and filtered off.

Yield: 880 mg (60%).

Melting point: 210°-212° C. (decomposition); $(\alpha)_D^{22}$: −35.9° (c=1, methanol).

Val: 0.95; Leu: 2.0; Lys: 0.95.

The compound is suitable as a substrate for the determination of plasmin and plasmin inhibitors.

EXAMPLE 6

Z-Ser-Arg-Leu-Phe-pNa 6.1 Z-Ser(O-But)-Arg-Leu-Phe-pNa.HBr 1.02 g (1.8 mmoles) of Z-Ser(O-But)-Arg-Leu-OH (prepared in accordance with the method of Chem-Ber. 107, 215–231 (1974)). 660 mg (1.8 mmoles) of H-Phe-pNa.HBr and 243 mg (1.8 mmoles) of HOBt are dissolved in 10 ml of dimethylformamide at 0° C. 370 mg (1.8 mmoles) of dicyclohexylcarbodiimide and 0.25 ml of N-ethylmorpholine are added to the solution and the reaction mixture is stirred at room temperature for 16 hours. The precipitate which has separated out is filtered off, the filtrate is evaporated to dryness, the residue is taken up in a little methanol and the product is precipitated with ether. The solid is dissolved again in methanol and a precipitate is then obtained with $NaHCO_3$ solution. Finally, the precipitate is dissolved in methanol and the solution is chromatographed over a LH 20 column using methanol as the mobile phase. The purified tetrapeptide-anilide fraction is collected.

Yield: 868 mg (53%); $(\alpha)_D^{22}$: −26.2° (c=1, methanol).

6.2. Z-Ser-Arg-Leu-Phe-pNa.HCl 100 mg (0.11 mmole) of Z-Ser(O-But)-Arg-Leu-Phe-pNa.HBr are dissolved in 5 ml of 1N HCl in glacial acetic acid, the solution is stirred at room temperature for 1 hour and concentrated and the product is precipitated with ether. After renewed dissolving and reprecipitating from methanol/ether and drying in vacuo over KOH, 72 mg of the tetrapeptide-anilide are obtained.

$(\alpha)_D^{22}$: −21.6° (c=1, methanol).

Ser: 0.88; Leu: 1.0; Phe: 0.95; Arg: 0.94.

The compound is suitable as a substrate for the determination of the clotting factor X.

EXAMPLE 7

Determination of kallikrein from plasma

The prekallikrein in plasma is determined via systemic activation of the clotting factor XII (Hageman factor), which activates prekallikrein to give kallikrein in a known manner. The substrate Boc-Gly-Pro-Leu-Gly-Arg-Leu-pNa, for example, can be used with the assistance of the aminopeptidase, for the enzymatic determination of the kallikrein.

Test batch for the determination of prekallikrein from plasma: 20 μl of plasma, 700 μl of buffer, 100 μl of factor XII activator*, 60 seconds incubation at 37° C., 20 μl of aminopeptidase and 200 μl of substrate (1.5 mmoles/l).

*PTT-reagent, clear, from Messrs.Behringwerke AG

Evaluation: ΔOD/minute×5,306.12=milli-units/ml of plasma=units/l of plasma.

EXAMPLE 8

Determination of prothrombin from plasma

The prothrombin content in plasma is determined, for example, via systemic activation with tissue thromboplastin (Thromborel®, Behringwerke). The clotting factors VII, X and V of the "extrinsic" system participate in the activation cascade, as is similar in the case of activation under physiological conditions. Compared with the state of the art, according to which prothrombin of any desired origin (including courmarin-induced prothrombin) is activated with ecarin (Eschiscarinatus snake venom), the system proposed in this case does not include modified prothrombin such as is formed by treatment with coumarin derivatives (oral anticoagulant therapy). Because of the specificity of the substrates according to the invention, the enzymatic factors of the cascade, for example F Xa, do not interfere with the determination. Examples of substrates which can be used are: H-D-Phe-Pro-Arg-Leu-pNa or Meoc-D-Phe-Pro-Arg-Leu-pNa.

Test batch for the determination of prothrombin from plasma: 10 μl of plasma, 200 μl of tissue thromboplastin, 3 minutes incubation at 37° C., 700 μl of buffer of pH 8.4, 20 μl of aminopeptidase and 150 μl of substrate (for example (B) 3 mmoles/l).

Evaluation: ΔOD/minute×5,561.2=milli-units/ml of plasma=units/l of plasma

We claim:

1. A compound of the formula

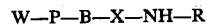

wherein W is $R_1CO—$ wherein $R_1$ is $C_1–C_6$ aliphatic hydrocarbon, $C_6–C_{10}$ aromatic hydrocarbon, $C_7–C_{10}$ araliphatic hydrocarbon; or $C_6–C_{10}$ alkaryl, or W is $R_2OCO—$ wherein $R_2$ is $C_1–C_6$ aliphatic hydrocarbon, $C_7–C_{10}$ araliphatic hydrocarbon, or alkyl$_{1–6}$ sulfonylalkyl$_{2–6}$, or W is benzenesulfonyl or $C_7–C_{10}$ alkarylsulfonyl;

P is valine, serine, Phe-Pro, Val-Glu-Gly, Val-Leu, Gly-Pro-Glu-Gly, or Ile-Glu-Gly, side chain groups of which may be substituted by protective groups;

B is arginine, lysine, phenylalanine, tyrosine, or homoarginine;

X is an L-amino acid selected from the group consisting of phenylalanine, tyrosine, valine, leucine, serine, glycine, and Leu-Phe, side chain groups of which may be substituted by protective groups; and R is an aromatic hydrocarbon, which may be substituted; wherein X—NH—R is a chromogenic group which is cleaved by hydrolytic enzymatic action to form a compound $H_2N$—R, the amount of which can be measured by photometric, spectrophotometric, or fluorescence-photometric methods.

2. A compound as in claim 1 wherein R is nitrophenyl, naphthyl, nitronanphthyl, methoxynaphthnyl, phenyl, methylnitrophenyl, dinitrophenyl, quinolyl, nitroquinolyl, or a salt thereof.

3. A compound as in claim 1 wherein R is nitrophenyl or is nitrophenyl substituted by halogen, trifluoromethyl, carboxyl, methoxy, sulfonic acid, or cyano.

4. A compound as in claim 1 wherein R is dimethoxycarbonylphenyl, pyridine, nitrobenzothiazole, pyrazine, triazole, benzopyrazole, chrysene, naphthyl, methoxynaphthyl, azulene, or aminocoumarin, which may be substituted.

* * * * *